United States Patent [19]

Müller et al.

[11] 4,428,035
[45] Jan. 24, 1984

[54] ELECTRONIC FLASHLIGHT FOR OPHTHALMOLOGICAL EXAMINATION INSTRUMENTS

[75] Inventors: Ortwin Müller, Aalen; Albrecht Vogel, Oberkochen, both of Fed. Rep. of Germany

[73] Assignee: Carl-Zeiss-Stiftung, Heidenheim, Fed. Rep. of Germany

[21] Appl. No.: 444,763

[22] Filed: Nov. 26, 1982

[30] Foreign Application Priority Data

Dec. 5, 1981 [DE] Fed. Rep. of Germany ... 8135489[U]

[51] Int. Cl.³ .............................................. F21S 3/00

[52] U.S. Cl. ..................................... 362/224; 362/17; 362/18; 362/223; 362/253; 362/293; 362/297; 362/307; 362/308; 362/319; 362/321; 362/328; 362/335; 362/350; 362/362; 362/804

[58] Field of Search .................. 362/17, 18, 223, 224, 362/253, 293, 297, 307, 308, 319, 321, 328, 335, 350, 362, 804

[56] References Cited

U.S. PATENT DOCUMENTS 3,900,858  8/1975  McCann et al. ................ 362/17 X
4,352,150  9/1982  Hosoda .......................... 362/217 X

*Primary Examiner*—Stephen J. Lechert, Jr.
*Attorney, Agent, or Firm*—Stonebraker, Shepard & Stephens

[57] ABSTRACT

This invention concerns an electronic flashlight for ophthalmological examination instruments.

5 Claims, 2 Drawing Figures

ELECTRONIC FLASHLIGHT FOR OPHTHALMOLOGICAL EXAMINATION INSTRUMENTS

BACKGROUND OF THE INVENTION

Ophthalmological examination instruments, e.g. operating microscopes and slit lights, have, as a rule, a lighting device inside the instrument for the process of examining the specimen. For making photographs, such examination instruments are most often provided with a mounting support for an electronic flashlight, the light of which falls on the examination specimen at such an angle to the optical axis of the viewing beam path that the specimen field illuminated by the electronic flash is substantially larger than the specimen field illuminated by the lighting device inside the instrument.

SUMMARY OF THE INVENTION

The invention has for its object the provision of improved flashlight apparatus wherein the light of the electronic flashlight will impact on the examination specimen as coaxially as possible to the optical axis of the viewing beam path, and will increase the intensity of illumination on the specimen.

According to the invention, this object is accomplished by providing a flashlight in which the light is located in a housing which can be attached under the main lens of the examination instrument, with openings arranged in the housing for the illumination and/or viewing beam path of the instrument, and wherein an electronic flash tube is arranged at one side of the main lens in the focus of an aspherical mirror, and at the other side of the main lens a reflector mirror is provided, which directs the flash emission radiated by the aspherical mirror onto the examination specimen as coaxially as possible to the optical axis of the viewing beam path, and by providing a condenser lens between the aspherical mirror and the reflector mirror, which condenser lens adapts the field of the flash emission to the instrument magnification.

When the aspherical mirror is in the shape of a paraboloid or of an ellipsoid, a rod-shaped electronic flashtube is used advantageously. The reflector mirror is most appropriately a flat mirror placed obliquely to the axis; it may also take the form of a deviating prism. For the purpose of adjusting to various instrument magnifications, collector lenses are advantageously provided, which can be inserted in the beam path of the electronic flashlight in front of the reflector mirror, e.g. on changing slide bars. The changing slide bar can be formed in such a manner that simultaneously with or also instead of a reflector lens, diaphragms and color filters can be inserted in the beam path.

The advantages obtained by the invention comprise particularly an increase in the intensity of illumination at the spot of the specimen, amounting to approximately 3.5 photographic diaphragm steps over comparable electrical excitation energies of an electronic flash without the device according to the invention. When the electronic flashlight according to the invention is attached to a slit light, it is possible, by way of attachment coaxially to the optical instrument axis, to place the unavoidable mirror image of the electronic flash tube on the front face of the cornea in the center of the pupil of the patient's eye, thereby satisfying methodological requirements of ophthalmologists.

BRIEF DESCRIPTION OF THE DRAWINGS

A form of embodiment of the invention is shown in the drawings, in which.

DESCRIPTION OF THE PREFERRED EMBODIMENTS

Figure 1:
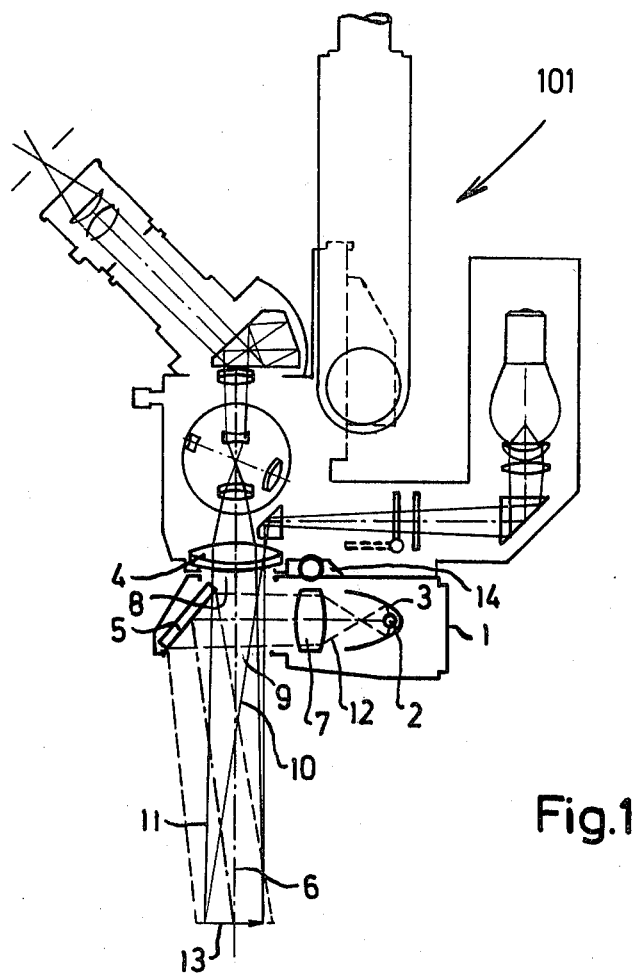
FIG. 1 shows an electronic flashlight according to the invention combined with an operating microscope.

In FIG. 1, the housing of the electronic flashlight is indicated at 1. In the focus of an aspherical mirror 3, a rod-shaped electronic flash tube 2 is arranged. The flash reflected by the aspherical mirror is directed in parallel by the lens 7 and encounters an obliquely arranged plane reflector mirror 5. The inclination of the reflector mirror 5 is selected in such a way that the flash will impact on the examination specimen at 13 nearly coaxially to the optical axis 6 of the ophthalmological examining instrument indicated in general at 101, such as a conventional operating microscope. The main lens of the instrument is shown at 4. In practice, the angle of incidence between the flash emission beam 12 and the optical axis 6 is about 4°. The cone of light inside the instrument marked 10 also falls normally on the examination specimen under this angle. The viewing beam path of the instrument is marked 11.

The housing 1 of the electronic flashlight can be connected to the body 101 of the examination instrument by attaching means indicated schematically at 14. At 8 and 9, the housing has openings for the viewing beam path 11 of the examination instrument.

Figure 2:
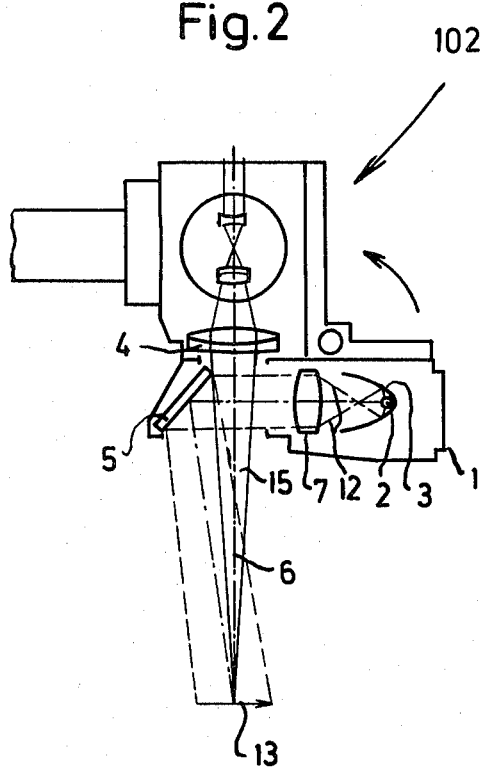
FIG. 2 shows an electronic flashlight according to the invention combined with a slit light.

FIG. 2 shows the flashlight of the invention attached to an ophthalmological examination instrument of the conventional slit type, here designated in general at 111. The illumination beam path of the slit lamp is indicated at 15, and its main lens at 4. For the parts of the flashlight, the same numerals are used as in FIG. 1.

We claim:

1. An electronic flashlight for attachment to and use with an ophthalmological examination instrument of the type having a main lens and an optical axis passing axially through said main lens, said flashlight comprising
   (a) a housing (1) adapted to be attached to said instrument under said main lens,
   (b) said housing having openings (8, 9) for passage therethrough of an illumination beam (10, 15),
   (c) an aspherical mirror (3) mounted in said housing on one side of said optical axis,
   (d) an electronic flash tube (2) mounted at a focal point of said aspherical mirror and arranged, when fired, to project a beam of light from said aspherical mirror in a direction across said optical axis to the opposite side of said axis,
   (e) a reflector mirror (5) mounted in the path of said beam on said opposite side of said axis and positioned to reflect said beam in a direction away from said main lens and approximately along said optical axis and converging toward said optical axis to intersect with the optical axis approximately at the location (13) of a specimen being examined, and
   (f) a condenser lens (7) mounted in said housing between said aspherical mirror (3) and said reflector mirror (5), said condenser lens being dimensioned to adapt the size of the field of illumination by the flashlight of the specimen being examined, to the magnification of the examination instrument.

2. The invention defined in claim 1, further comprising various collector lenses arranged on a selectively movable support, for adapting the size of the field illuminated by the flashlight to various different magnifications of the examination instrument.

3. The invention defined in claim 2, further comprising iris diaphragm means and color filter means arranged in said beam path to minimize corneal reflection.

4. The invention defined in claim 1, wherein said examination instrument is an operating microscope.

5. The invention defined in claim 1, wherein said examination instrument is a slit light.

* * * * *